(12) United States Patent
Cohen

(10) Patent No.: US 8,968,207 B2
(45) Date of Patent: Mar. 3, 2015

(54) METHODS AND APPARATUS FOR VISUALLY REPRESENTING A CARDIAC STATUS OF A PATIENT

(75) Inventor: Richard J. Cohen, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 571 days.

(21) Appl. No.: 12/601,027

(22) PCT Filed: Apr. 13, 2009

(86) PCT No.: PCT/US2009/040299
§ 371 (c)(1),
(2), (4) Date: Feb. 16, 2010

(87) PCT Pub. No.: WO2009/129158
PCT Pub. Date: Oct. 22, 2009

(65) Prior Publication Data
US 2010/0249612 A1    Sep. 30, 2010

Related U.S. Application Data

(60) Provisional application No. 61/045,063, filed on Apr. 15, 2008.

(51) Int. Cl.
*A61B 5/02* (2006.01)
*A61B 5/029* (2006.01)
*A61B 5/021* (2006.01)

(52) U.S. Cl.
CPC .. *A61B 5/029* (2013.01); *A61B 5/021* (2013.01
USPC ........................................ 600/485; 600/481 )

(58) Field of Classification Search
USPC .................................................. 600/481–490
See application file for complete search history.

(56) References Cited

U.S. PATENT DOCUMENTS

| | | | |
|---|---|---|---|
| 5,674,256 A | 10/1997 | Carlson | |
| 5,687,733 A | 11/1997 | McKown | |
| 6,112,119 A | 8/2000 | Schuelke et al. | |
| 7,206,162 B2 | 4/2007 | Semba et al. | |
| 2004/0158163 A1* | 8/2004 | Cohen et al. | 600/508 |
| 2005/0240087 A1 | 10/2005 | Keenan et al. | |
| 2007/0197921 A1 | 8/2007 | Cohen et al. | |
| 2008/0287812 A1* | 11/2008 | Parlikar et al. | 600/485 |

OTHER PUBLICATIONS

Hamilton, W. F. et al., The Measurement of the stroke volume from the pressure pulse, American Journal of Physiology, vol. 148, pp. 14-24, 1947.

(Continued)

*Primary Examiner* — Patricia Mallari
*Assistant Examiner* — Tiffany Weston
(74) *Attorney, Agent, or Firm* — Cooley LLP

(57) ABSTRACT

Method and apparatus are provided for computing signals related to cardiac output from physiologic input signals related to circulatory pressures or flows. Method and apparatus are provided for constructing a transforming filter and applying said filter to the physiologic input signals in order to obtain a signal proportional to phasic cardiac output or time-averaged cardiac output. This invention provides a means for real-time monitoring of cardiac output and stroke volume which is of great clinical importance but not otherwise feasible by present techniques.

66 Claims, 2 Drawing Sheets

(56) References Cited

OTHER PUBLICATIONS

Herd, J. A. et al., Arterial Pressure Pulse Contours during Hemorrhage in Anesthetized dogs, J. Applied Physiology, vol. 21, pp. 1864-1868, 1996.

Kouchokos, T. K. et al., Estimation of Stroke Volume in the Dog by a Pulse Contour Method, Circulation Research, vol. 26, pp. 611-623, 1970.

Warner, H. R. et al., Quantitation of Beat-to-Beat Changes in Stroke Volume from the Aortic Pulse Contour in Man, Journal of Applied Physiology, vol. 5, pp. 495-507, 1953.

Bourgeois, M. J. et al., Continuous Determination of Beat-to-Beat Stroke Volume from Aortic Pressure Pulses in the Dog, Circulation Research, vol. 39, pp. 15-24, 1976.

Welkowitz, W. et al., Noninvasive Estimation of Cardiac Output, IEEE Transactions in Biomedical Engineering, vol. 38, pp. 1100-1105, 1991.

Cappello, A., Comments on Noninvasive Estimation of Cardiac Output, IEEE Transactions on Biomedical Engineering, vol. 40, pp. 504-505, 1993.

Swamy, G. et al., Blind Identification of the Aortic Pressure waveform from multiple peripheral artery pressure waveforms, Am. J. Physiol. Heart Circ. Physiol., vol. 292, pp. H2257-2264, 2007.

Lu, Z. et al., Continuous cardiac output monitoring in humans by invasive and noninvasive peripheral blood pressure waveform analysis, J. Appl. Physiol., vol. 101, pp. 598-608, 2006.

Mukkamala, R. et al., Continuous Cardiac Output Monitoring by Peripheral Blood Pressure Waveform Analysis, IEEE Trans. Biomed. Eng., vol. 53, pp. 459-467, 2006.

Mukkamala, R. et al., Estimation of Arterial and Cardiopulmonary total Peripheral resistance baroreflex gain values: Validation by chronic arterial baroreceptor denervation, Am. J. Physiol. Heart Circ. Physiol., vol. 290, pp. H1830-H1836, 2005.

Mukkamala, R. et al., Cardiac Output Monitoring in Intensive Care Patients Radial Artery Pressure Waveform Analysis, Conf. Proc. IEEE Eng. Med. Biol. Soc., pp. 3712-3715, vol. 5, 2004.

Schoenberg, A. A. et al., Stroke Volume estimation from aortic pressure with correction for arrhythmias, J. of Cardiology, vol. 2, pp. 55-65, 1974.

Wesseling, K.H. et al., Beat to Beat cardiac Output from the Arterial Pressure Pulse Contour, Measurements in Anesthesia, pp. 150-164, Leiden University Press, 1974.

PCT International Search Report, Application No. PCT/US09/040299, Dec. 6, 2009.

* cited by examiner

METHODS AND APPARATUS FOR VISUALLY REPRESENTING A CARDIAC STATUS OF A PATIENT

This application claims the benefit, under 35 U.S.C. §371, as a national stage application of International Application No. PCT/US2009/040299, filed Apr. 13, 2009, which claims the benefit of U.S. Provisional Patent Application Ser. No. 61/045,063, filed Apr. 15, 2008. The contents of each of the above-identified applications are incorporated herein by reference in their entirety.

A Computer Program Listing Appendix (147,456 bytes) was created on Nov. 11, 2014, and submitted in duplicate on two identical compact discs. The contents of the Computer Program Listing Appendix were present in PCT/US2009/040299 and are incorporated herein by reference in their entirety.

BACKGROUND OF THE INVENTION

Cardiac output, or total blood flow to the periphery, is perhaps one of the most vital quantities to be able to monitor in a critically ill patient. A decrease in cardiac output may be one of the first indicators of a deterioration in circulatory function. Conversely, an increase in cardiac output may indicate the beneficial effect of a therapeutic intervention. The arterial blood pressure which is often monitored in intensive care unit patients provides a poor indication of cardiac output because of the body's extensive feedback system which can maintain arterial blood pressure in a narrow range despite wide variations in cardiac output.

There are currently a number of technologies for determining cardiac output: thermodilution, dye dilution, ultrasound and bioimpedance. Although these technologies can provide useful information, they have a number of shortcomings as discussed below.

At present thermodilution is the standard technique for measuring cardiac output in critically ill patients. Thermodilution measurements are conducted in the following manner. A catheter is advanced through a peripheral vein into the vena cava, through the right heart and into the pulmonary artery. A bolus of chilled fluid is then injected into the catheter and emerges from an upstream port in the catheter. The blood temperature is recorded at a downstream thermistor embedded in the catheter. Cardiac output is then determined from a numerical analysis of the time evolution of the blood temperature.

Thermodilution has several disadvantages:
  (1) It requires the placement of a pulmonary artery catheter—this is a non-trivial invasive procedure and is not feasible in all patients, e.g. newborn infants. This procedure is also very expensive and time and personnel intensive.
  (2) The measurement is not continuous in time—and generally is at most repeated every few hours.
  (3) The measurement is not always accurate, especially in low blood flow conditions.

Dye dilution techniques are sometimes used in the intensive care unit setting. This technique is also noncontinuous and personnel intensive. This technique requires venous injection of a dye and measurement of the dye dilution in a series of arterial blood samples drawn from an arterial catheter.

Similarly, oxygen consumption (Fick) methods are also used occasionally in the cardiac catheterization laboratory. This method involves simultaneous measurement of central venous and arterial oxygen content of blood and measurement of ventilatory oxygen uptake (oxygen consumption). This cumbersome method is regularly used only in the catheterization laboratory.

Ultrasound techniques for measuring cardiac output generally rely upon the measurement of the Doppler shift in the frequency of an ultrasound beam reflected from the flowing aortic blood. This technique suffers from the difficulty in stabilizing an external ultrasound transducer, the need to assume a cross-sectional flow profile of the blood in the aorta, and the uncertainty in the angle between the ultrasound beam and the aorta.

The Transonic Systems Flowmeter (Ithaca, N.Y.) utilizes an ultrasound transit-time principle to measure flow, but is not practical for routine clinical use, because it is highly invasive requiring the placement of a transducer directly around the aorta. Conventional electromagnetic flowmeters are also not practical for routine clinical use because they also require placement of a transducer directly around the aorta.

Bioimpedance techniques involve measuring changes in the electrical impedance of the thorax during the cardiac cycle. Bioimpedance changes are only indirectly related to changes in cardiac flow and are especially unreliable in patients with cardiovascular or respiratory illnesses in which the electrical impedance properties of the thorax are altered.

A continuous cardiac output monitor would be of great practical value in the management of intensive care unit patients, patients in the operating and recovery rooms, as well as patients undergoing cardiac catheterization. Such a device would provide the physician with immediate feedback on the outcome of different interventions such as varying infusion rates of cardioactive and vasoactive drugs, infusion rates of intravenous fluids, ventilator settings, etc.

It would be very advantageous to have a device which could monitor cardiac output by analyzing a systemic artery or pulmonary artery blood pressure signal, or other physiologic signal related to circulatory pressures or flows. It would be desirable for such a device to be able to compute a quantity proportional to stroke volume for each heart beat, a signal proportional to the phasic cardiac output flow signal (the phasic cardiac output signal is a signal with sufficient time resolution to reflect variations in flow within a single cardiac cycle), a signal proportional to the time-averaged cardiac output (the time-averaged cardiac output reflects the cardiac output averaged over several heart beats), and/or a quantity proportional to the current value of the vascular resistance. It would be desirable for such a device to be able to use as input the amplified arterial blood pressure signal from an existing bedside monitor. The blood pressure transducer used could be an arterial catheter placed in essentially any arterial vessel—in particular in the radial artery or other peripheral arteries. Peripheral arterial catheters are very often in place in intensive care unit patients, and placing a peripheral arterial line is a relatively simple procedure. This device optimally could also utilize as input the pulmonary artery pressure recorded from a pulmonary artery catheter. In addition, it would be desirable for such a device to be able to use as input other physiologic waveforms related to circulatory pressures or flows. These might include continuous noninvasive blood pressure monitor signals, measurements of the optical density or reflectance of peripheral tissue using photoelectric sensors and measurement of fluctuations in peripheral tissue pressures, etc.

Many investigators have attempted to analyze the arterial blood pressure waveform in order to compute beat-to-beat stroke volume (see for example, W. F. Hamilton and J. W. Remington, "The Measurement of Stroke Volume from the Pressure Pulse," American Journal of Physiology, Volume 148, pp 14-24, 1947; J. A. Herd, N. R. LeClair and W. Simon, "Arterial Presure Pulse Contours during Hemmorrhage in Anesthetized Dogs," J. Applied Physiology, Volume 21, pp 1864-1868,1966; T. K. Kouchokos, B. S. Sheppard and D. A. McDonald, "Estimation of Stroke Volume in the Dog by a Pulse Contour Method," Circulation Research, Volume 26, pp 611-623, 1970; A. A. Schoenberg, U. Mennicken, R. Simon, P. Brambring and P. H. Heintzen, "Stroke Volume estimation for Aortic Pressure with Correction for Arrhythmias," Journal of Cardiology, Volume 2, pp 55-65, 1974; H. R. Warner, H. J. C. Swan, D. C. Connolly, R. G. Tompkins, and E. H. Wood, "Quantitation of Beat-to-Beat Changes in Stroke Volume from the Aortic Pulse Contour in Man," Journal of Applied Physiology, Volume 5, pp 495-507, 1953; K. H. Wesseling, N. T. Smith, W. W. Nicholis, B. de Wit and J. A. P Weber, "Beat-to-Beat Cardiac Output from Arterial Pressure Pulse Contour," in Measurements in Anesthesia, Feldamn, Leight and Spierdijk, Eds, Leiden: Leiden Universary Press, 1974). These attempts were for the most part based on semi-empirical mathematical formulas, and failed to yield good correlation between stroke volume derived from analysis of the arterial pressure waveform and true stroke volume over a range of physiologic conditions. Bourgeois et al (M. J. Bourgeois, B. K. Gilbert, G. von Bernuth, and E. H. Wood, "Continuous Determination of Beat-to-Beat Stroke Volume from Aortic Pressure Pulses in the Dog", Circulation Research, Volume 39, 1976, pp 15-24) did successfully demonstrate in animal studies that analysis of the aortic blood pressure waveform based on a parallel resistor-capacitor circuit of the peripheral circulation yielded could yield a quantity which varied linearly with the stroke volume measured using an electromagnetic flowmeter over a wide range of physiologic conditions.

However, the method of Bourgeois et al only worked when the diastolic decay of the aortic blood pressure waveform was described by a perfect exponential function. In the animal studies this was accomplished by varying the position of the aortic blood pressure monitoring catheter until a location was found in the central aorta where the decay was indeed exponential. Clinically, because of the risk of blood clot formation and embolization it is not practical to leave an aortic catheter in place. Arterial pressure is generally measured using a peripheral arterial recording—usually in the radial artery. The arterial blood pressure waveform is distorted as it propagates through the arterial tree and the diastolic decay is generally very non-exponential by the time it reaches peripheral arteries. The method of Bourgeois fails when a peripheral arterial trace is used as input, thus rendering the technique useless from a clinical point of view. Moreover, the method of Bourgeois suffers from several other defects. The method of Bourgeois provides a measure proportional to stroke volume for each beat but does not provide the actual phasic cardiac output signal. The waveform of the phasic cardiac output signal could provide important information regarding cardiac contractility. Finally, the method of Bourgeois et al is dependent on the accurate determination of the end of systole for each beat. Bourgeois et al attempted to accomplish this determination by analysis of the dicrotic notch of the central aortic waveform. This method for the determination of the end of systole may be inaccurate, particularly for peripheral arterial pressure traces where the dicrotic notch may be shifted, distorted or absent.

Welkowitz et al (W. Welkowitz, Q. Cui, Y. Qi, and J. B. Kostis, "Noninvasive Estimation of Cardiac Output", IEEE Transactions in Biomedical Engineering, Volume 38, pp. 1100-1105, 1991) utilized an adaptive aorta model in conjunction with carotid and femoral measurements to estimate cardiac output. This method suffers from a number of defects. It requires two simultaneous pressure measurements. At one of the sites (carotid artery) one cannot safely place a catheter, rendering continuous monitoring of arterial pressure and thus cardiac output impossible; the second site (femoral artery) also is not suitable for leaving an arterial catheter in place for prolonged periods or otherwise continuously measuring arterial pressure at this site. The adaptive aortic model contains a very specific model and limited model of the circulation which is not physiologically accurate, with multiple parameters which cannot be adequately fit with experimental data (see for example, A. Cappello and A. Cardaioli, 'Comments on "Noninvasive Estimation of Cardiac Output", IEEE Transactions on Biomedical Engineering, Volume 40, 1993, pp 504-505).

More recently a method for measuring cardiac output has been developed by measuring the impulse response function between cardiac contractions and the arterial blood pressure waveform (Mukkamala R, Kuiper J, Ahmad S, Lu Z. Cardiac output monitoring in intensive care patients by radial artery pressure waveform analysis. Conf Proc IEEE Eng Med Biol Soc. 2004; 5:3712-3715; Swamy G, Ling Q, Li T, Mukkamala R. Blind identification of the aortic pressure waveform from multiple peripheral artery pressure waveforms. Am J Physiol Heart Circ Physiol. 2007; 292(5):H2257-2264; Lu Z, Mukkamala R. Continuous cardiac output monitoring in humans by invasive and noninvasive peripheral blood pressure waveform analysis. J Appl Physiol. 2006; 101(2):598-608; Mukkamala R, Reisner A T, Hojman H M, Mark R G, Cohen R J. Continuous cardiac output monitoring by peripheral blood pressure waveform analysis. IEEE Trans Biomed Eng. 2006; 53(3):459-467; Mukkamala R, Kim J K, Li Y, Sala-Mercado J, Hammond R L, Scislo T J, O'Leary D S. Estimation of arterial and cardiopulmonary total peripheral resistance baroreflex gain values: validation by chronic arterial baroreceptor denervation. Am J Physiol Heart Circ Physiol. 2006; 290(5):H1830-1836; United States Patent Application 20040158163 Methods and apparatus for determining cardiac output; United States Patent Application 20070197921 Methods and apparatus for determining cardiac output and left atrial pressure). However, this method does not provide a continuous signal proportional to cardiac output nor does it provide a means for estimating stroke volume on a beat-to-beat basis.

What is needed is a reliable accurate means of measuring a stroke volume, phasic cardiac output, time-averaged cardiac output and vascular resistance from systemic arterial pressure traces, pulmonary artery traces or other physiologic signals.

SUMMARY OF THE INVENTION

The present invention involves methods for computing cardiac output signals and vascular resistances from physiologic input signals related to circulatory pressures and flows. One preferred embodiment of the present invention involves the measurement of a physiologic input signal related to circulatory pressures or flows, constructing a transforming filter to transform the physiologic input signal into a signal proportional to phasic cardiac output, and then applying that filter to the physiologic input signal to compute a signal proportional to cardiac output. Here a filter is understood to be a device, process or method that converts an input signal into an output signal. For example, a filter may represent a physical device, such as an electric circuit, that converts an input signal into an output signal, or an implementation of a computer algorithm that converts an input signal into an output signal. The phasic cardiac output reflects the variation in flow within individual cardiac cycles. The method of the invention may also be adapted to compute a signal proportional to the time-averaged cardiac output which reflects the cardiac output averaged over multiple beats. The method of the invention may also be adapted to compute a sequence of numbers proportional to the stroke volumes of a sequence of cardiac cycles, by integrating the cardiac output over at least the periods corresponding to the systolic portion of each cardiac cycle. In one preferred embodiment the transforming filter is constructed so that when it is applied to the physiologic input signal, the output signal is reduced during the periods of time corresponding to cardiac diastole, subject to a normalization constraint on the gain of the transforming filter. In one preferred embodiment the physiologic input signal is an arterial or pulmonary pressure, and the constraint is that the dc gain of the transforming filter is inversely proportional to the contemporary value of the corresponding systemic or pulmonary vascular resistance. In one preferred embodiment of the invention a method is used for calculating the systemic or pulmonary vascular resistance from a physiologic input signal related to the systemic or pulmonary pressures or flows. This method involves applying a filter, of known form which depends on a quantity related to the vascular resistance, to the physiologic input signal and then adjusting the quantity related to the vascular resistance to reduce the width of the filtered waveforms corresponding to one or more cardiac cycles. In one preferred embodiment a computed cardiac output signal may be normalized by using one or more independent measurements of absolute cardiac output.

DESCRIPTION OF THE PREFERRED EMBODIMENT

Figure 1:
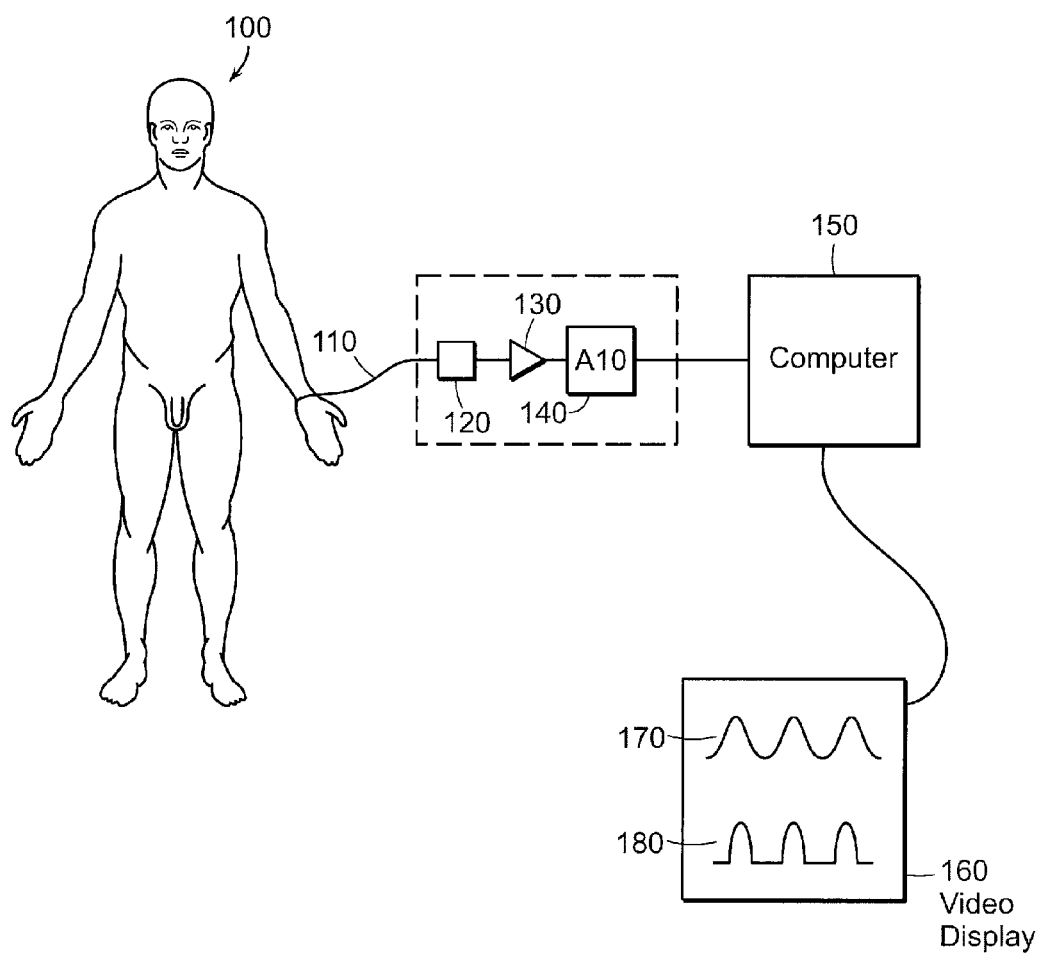
FIG. 1 is a schematic illustration of a preferred embodiment of the invention.

FIG. 1 is an illustration of a preferred embodiment of the invention. 100 is a human patient. 110 is a fluid filled catheter inserted into the radial artery of the patient used to measure the phasic arterial blood pressure. 120 is a transducer which converts the pressure in the fluid in the catheter into an electrical signal. 130 is an electronic amplifier to increase the voltage of the electrical signal and to condition the signal. 140 is an analog to digital converter which is an electronic device used to convert the electrical signal into digital form. 150 is a computer which is used to construct a transforming filter to transform the physiologic input signal into a signal proportional to phasic cardiac output, and is used to apply the transforming filter to the physiologic input signal to compute a signal proportional to phasic cardiac output. 160 is a video screen. 170 is a display of the original phasic arterial blood pressure signal. 180 is a display of the computed signal proportional to phasic cardiac output.

Figure 2:
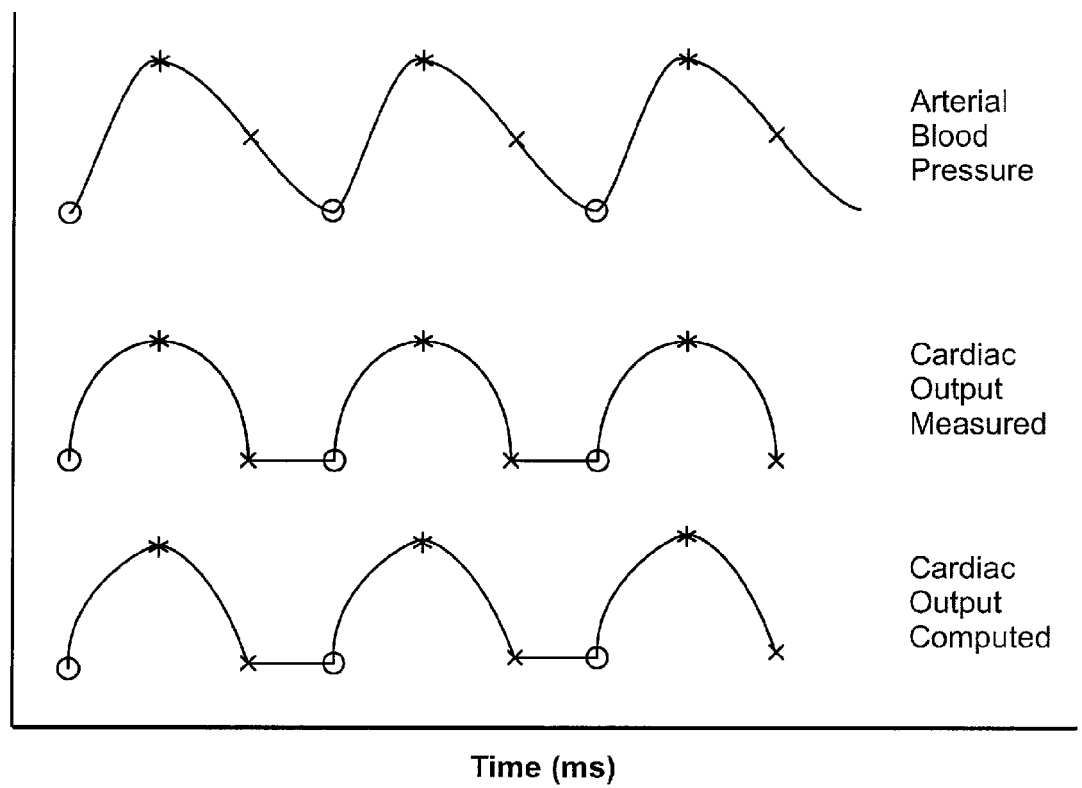
FIG. 2 is a plot of three signals vs. time measured in milliseconds which illustrate the application of the method of the invention.

FIG. 2 is a plot of three signals versus time measured in milliseconds which illustrate the application of the method of the invention. The top trace is a peripheral arterial blood pressure signal measured in a limb of an experimental animal. The ordinate is measured in units of millimeters of mercury. The open circles designate the times corresponding to the end of diastole and the onset of systole. The asterisks mark the times of peak systolic pressure. The crosses designate the times corresponding to the end of systole and the onset of diastole. The location of the open circles, the asterisks and the crosses were computed automatically by a computer program. The middle trace is a phasic cardiac output signal (in arbitrary units) directly measured experimentally using a Transonic Systems ultrasonic flow probe which was surgically placed around the animal's proximal aorta. Notice that the phasic cardiac output signal consists of pulses of flow during the periods of systole and that the measured flow is essentially zero during periods of diastole. The bottom tracing is the phasic arterial blood pressure signal computed by the method of the invention from the arterial blood pressure signal shown in the top trace. Notice that the shape of the waveforms correspond closely to those of the directly measured phasic cardiac output signal in the middle trace. Notice that the phasic arterial blood pressure signal computed according to the method of the invention also becomes essentially zero during periods of diastole.

The present invention involves methods for computing cardiac output signals and vascular resistances from physiologic input signals related to circulatory pressures and flows. It is understood that the cardiac output signals and vascular resistances computed according to the methods of this invention are only approximations to the true cardiac output and vascular resistances, but that the approximations are sufficiently accurate to be of clinical utility and are valuable because they may be computed using readily available physiologic signals. One preferred embodiment of this invention involves computing a signal proportional to phasic cardiac output by measuring a physiologic input signal related to circulatory pressures or flows. Examples of suitable physiologic input signals include either a central or peripheral systemic arterial pressure. A peripheral systemic artery pressure may be measured, for example, using an intra-arterial catheter in a peripheral artery (see FIG. 1) or by using a noninvasive transducer such as a finger plethysmograph, or a pulmonary artery pressure measured by an intravascular catheter, or a measure of the volume of the ear lobe obtained by measuring the optical, or infra-red, density of the earlobe or by other means. The pulmonary or systemic arterial signals may be measured with respect to a variety of possible reference pressures such as atmospheric pressure, central venous pressure, pulmonary venous pressure, esophageal pressure or pressures measured in other intrathoracic locations. A transforming filter is constructed to transform the physiologic input signal into a signal proportional to phasic cardiac output. The phasic cardiac output signal corresponds to the flow across the aortic or pulmonary valves and is defined to be represented with sufficient time resolution to reflect the variation in flow within individual cardiac cycles. The transforming filter is applied to the physiologic input signal to compute a signal proportional to phasic cardiac output (see FIG. 2).

In one preferred embodiment the transforming filter is constructed so that when the transforming filter is applied to the physiologic input signal, the phasic cardiac output signal is reduced during periods of time corresponding to cardiac diastole, subject to a normalization condition on the gain of the transforming filter. Since the phasic cardiac output corresponds to flow across the aortic or pulmonic valves, the phasic cardiac output should be zero during cardiac diastole which is the phase of the cardiac cycle during which these valves are closed. (It is understood here that since physiologic input signals may incorporate a time delay and that the phases of the cardiac cycle, such as diastole and systole, may be defined relative to the physiologic input signal and thus may be time shifted with respect to the actual phases of the cardiac cycle in the heart). This preferred embodiment will be less effective in the presence of regurgitant diastolic flow across a diseased aortic valve when the input physiologic signal is a systemic arterial pressure, or a physiologic signal related to systemic arterial pressure. This preferred embodiment will be less effective in the presence of regurgitant diastolic flow across a diseased pulmonic valve when the input physiologic signal is a pulmonary arterial pressure, or a physiologic signal related to pulmonary arterial pressure. A constraint on the normalization of the transforming filter is required so that magnitude of the computed flow during cardiac systole is appropriately maintained as the transforming filter is adjusted to reduce flow during cardiac diastole. Without such a normalization constraint, one might—for example—construct a trivial filter whose output is always zero.

In one preferred embodiment the physiologic input signal is a systemic or pulmonary arterial pressure, and the transforming filter is constructed so as to reduce the phasic cardiac output signal during cardiac diastole subject to a normalization constraint that the dc gain of the transforming filter be inversely proportional to the contemporary value of the corresponding systemic or pulmonary vascular resistance. In this embodiment the normalization constraint requires that the dc gain of the transforming filter be inversely proportional to the vascular resistance of the system or pulmonary vascular bed. This approach is appropriate since the vascular resistance changes slowly (typically on a time scale greater than 20 seconds) with respect to the length of a heart beat (typically less than one second). Thus the vascular resistance can be considered to be time invariant on the time scale of one heart beat. The time averaged cardiac output multiplied by the vascular resistance should equal the pressure drop across the vascular bed. This pressure drop may be approximated by the systemic arterial pressure in the case of the systemic vascular bed or the pulmonary arterial pressure in the case of the pulmonary vascular bed. The method of this embodiment may be more accurate if the systemic arterial pressure is measured with reference to the central venous pressure or an approximation thereto, or if the pulmonary arterial pressure is measured with respect to the pulmonary venous pressure or an approximation thereto.

In one preferred embodiment of this invention a quantity related to systemic or pulmonary vascular resistance is computed by measuring a physiologic input signal related to systemic or pulmonary circulatory pressures or flows, constructing a filter in which the quantity is a parameter, applying the filter to the physiologic input signal over one or more cardiac cycles, and adjusting the quantity to reduce the width of the filtered output waveform or waveforms corresponding to the one or more cardiac cycles. As shown in Example 1, with appropriate design of the filter the method of this embodiment will lead to an accurate determination of the magnitude of this quantity. In particular in Example 1 a preferred embodiment is presented in which the filter used is the functional inverse of the expected cardiac output to central pressure transfer relation. Example 1 illustrates this embodiment in the case where the filter used is the functional inverse of an exponentially decaying impulse-response function, whose time constant is a quantity which is proportional to the vascular resistance. As shown in Example 1, in one preferred embodiment this filter is defined by the equation, $y(i)=x(i)-\alpha x(i-1)$, where $x(i)$ and $x(i-1)$ denote the i'th and (i-1)'th sampled values of the physiologic input signal and $\alpha$ is a quantity related to vascular resistance. In the case of this last preferred embodiment it is shown in Example 1 that the width of the filtered output waveform or waveforms to be reduced by adjusting the quantity $\alpha$ is given by the formula:

$$w = \frac{\sum_i g1(i)g2(P^a(i) - \alpha P^a(i-1))}{\sum_i g2(P^a(i) - \alpha P^a(i-1))}$$

where the sum over the index i starts at a point corresponding to the beginning of systole in the cardiac cycle, and g1 and g2 are increasing functions of their arguments.

In one preferred embodiment one computes from the value of the quantity related to the systemic or pulmonary vascular resistance the value of a quantity proportional to the systemic or pulmonary vascular resistance. This may be accomplished by applying a known functional relationship between the quantity proportional to the systemic or pulmonary vascular resistance and the quantity related to the systemic or pulmonary vascular resistance.

In one preferred embodiment one uses the contemporary value of the quantity related to the systemic or pulmonary vascular resistance to determine the dc gain of the transforming filter. This may be accomplished, for example, by setting the gain of the transforming filter to be inversely proportional to the quantity proportional to the systemic or vascular resistance which is derived from the quantity related to the systemic or pulmonary vascular resistance. This preferred embodiment is illustrated in Example 1.

In one preferred embodiment the transforming filter used to transform the physiologic input signal to the phasic cardiac output signal is a linear filter whose coefficients are adjusted over time. This preferred embodiment is illustrated in Example 1.

In one preferred embodiment the transforming filter is a linear filter whose coefficients are adjusted over time, subject to a normalization constraint on the gain of the filter, so that when the transforming filter is applied to a physiologic input signal the transforming filter's output is reduced during cardiac diastole. This preferred embodiment is illustrated in Example 1.

In one preferred embodiment the transforming filter is the convolution of two filters: a first filter representing the transformation of the physiologic input signal to a central pressure signal and a second filter representing the transformation of the central pressure signal to a cardiac output signal. This procedure is illustrated in Example 1 for a case where the dc gain of the first filter is constant and the second filter is of known form depending on the vascular resistance.

In one preferred embodiment the transforming filter is the convolution of two filters: a second filter of the form $y(i)=x(i)-\alpha x(i-1)$ where $\alpha$ is adjusted over time with changes in the vascular resistance; and a first filter whose coefficients are adjusted over time, subject to the constraint that the dc gain of the first filter is constant, to reduce the transforming filter's output during diastole when the transforming filter is applied to the physiologic input signal. This preferred embodiment is illustrated in Example 1.

In one preferred embodiment a sequence of numbers proportional to the stroke volumes of a sequence of cardiac cycles are calculated by applying the transforming filter to the physiologic input signal to obtain a signal proportional to phasic cardiac output, and then integrating this signal over at least the periods corresponding to the systolic portion of each of the cardiac cycles in the sequence to generate a sequence of numbers proportional to the stroke volumes.

One preferred embodiment involves computing the signal proportional to the phasic cardiac output by applying the transforming filter to the physiologic input signal and displaying the signal proportional to phasic cardiac output, for example on a video display screen.

One preferred embodiment involves computing the signal proportional to the phasic cardiac output by applying the transforming filter to the physiologic input signal and displaying in real-time the signal proportional to phasic cardiac output, for example on a video display screen. This would be of great advantage in that physicians and nurses could immediately observe changes in the phasic cardiac output. A change in a patient's status could then be rapidly detected and appropriate medical intervention could be initiated.

In one preferred embodiment the computed signal proportional to phasic cardiac output may be normalized by using one or more determinations of cardiac output by an independent method. For example, one could perform a one-time measurement of cardiac output by the thermodilution method, and one could simultaneously measure an average of the computed signal proportional to the phasic cardiac output over the period during which the thermodilution measurement was made, and thereby determine a calibration constant which when multiplied by the signal proportional to phasic cardiac output yields a signal equal to phasic cardiac output. This preferred embodiment would be most useful in situations where it is desirable to know the absolute phasic cardiac output of a patient.

In one preferred embodiment the time-average of the signal proportional to phasic cardiac output is computed to obtain a signal proportional to the time-averaged cardiac output. This preferred embodiment would be most useful in situations where it is desirable to measure long term changes in cardiac output.

One preferred embodiment involves computing a signal proportional to the time-averaged cardiac output, by measuring a physiologic input signal related to circulatory pressures or flows; constructing a transforming filter to transform the physiologic input signal into a signal proportional to phasic cardiac output; time-averaging the physiologic input signal; applying the transforming filter, or applying a modified form of the transforming filter suitable for use with a time-averaged physiologic input signal, to the time-averaged physiologic input signal to compute a signal proportional to the time-averaged cardiac output.

One preferred embodiment involves computing a time-averaged cardiac output signal comprising measuring a systemic or pulmonary pressure signal, time-averaging the pressure signal, and dividing the time-averaged pressure signal by the contemporaneous value of a quantity proportional to the corresponding systemic or pulmonary vascular resistance. A preferred embodiment for calculating a quantity proportional to the systemic or pulmonary vascular resistance is described above.

Another preferred embodiment for computing a time-averaged cardiac output signal comprising measuring a systemic or pulmonary pressure signal, dividing the pressure signal with the contemporary value of a quantity proportional to the corresponding systemic or pulmonary vascular resistance computed according to one of the methods described above, and time-averaging the resulting signal.

One preferred embodiment involves computing a time-averaged cardiac output signal by one of the methods described above and displaying the time-averaged cardiac output signal, for example on a video display screen. This preferred embodiment would be most useful in situations where it is desirable to monitor changes in cardiac output.

One preferred embodiment involves computing a time-averaged cardiac output signal by one of the methods described above and displaying in real-time the time-averaged cardiac output signal, for example on a video display screen. This would be of great advantage in that physicians and nurses could immediately observe changes in the phasic cardiac output. A change in a patient's status could then be rapidly detected and appropriate medical intervention could be initiated.

One preferred embodiment involves computing the time-averaged cardiac output by any of the methods described above normalizing the computed signal proportional to the time-averaged cardiac output by using one or more independent methods of measuring absolute cardiac output. This preferred embodiment can be most useful in situations where it is desirable to know the absolute time-averaged cardiac output.

One preferred embodiment involves computing a signal proportional to vascular resistance by repeatedly applying the one of the methods described above to sequential epochs of one or more cardiac cycles.

One preferred embodiment involves computing a signal proportional to vascular resistance as described above and displaying the signal proportional to vascular resistance, for example on a video screen. This preferred embodiment would be most useful in situations where it is useful to monitor changes in vascular resistance, so that nurses and physicians could immediately detect changes in vascular resistance, and intervene appropriately.

To reduce the output of the transforming filter during diastole, the diastolic period must be identified. In one preferred embodiment the onset of systole is taken to be the point of onset of the rapid systolic change in the physiologic input signal. The onset of diastole is determined by applying a formula relating the onset of diastole to the times of onset of preceding and/or following systoles. The end of diastole is approximately the onset of the following systole. This preferred embodiment is illustrated in Example 1.

In another preferred embodiment the transforming filter involves a non-linear transformation of the input signal.

EXAMPLE 1

In this example (see FIG. 1), the input signal is a central or peripheral arterial signal recorded by means of an indwelling catheter or a noninvasive continuous arterial blood pressure transducer. In the case of a fluid filled catheter (110) placed, for example, in the radial artery of a patient (100) the catheter is interfaced with a transducer (120) which converts the pressure in the fluid in the catheter into an electrical signal. This electrical signal is amplified and conditioned by means of an electronic amplifier (130). This amplifier may be incorporated in an existing bedside monitor which interfaces with the appropriate blood pressure sensor. The amplified and conditioned electrical signal is converted into digital form by means of an analog to digital converter (140). A digital computer (150) is used to construct a transforming filter and to apply this filter to the input signal in order to compute an output signal proportional to the phasic cardic output. A video screen (160) may be used to generate a display of the original arterial blood pressure signal (170) and a display the computed phasic cardiac output signal (180). It should be understood that the apparatus of this invention may incorporate in one instrument some or all of the components 120, 130, 140, 150, 160, 170, 180.

The amplified electrical blood pressure signal is then passed through suitable anti-aliasing filters and digitally sampled at 100 Hz. All the following manipulations of the signal are implemented in a computer program.

Let J be the flow across the aortic valve. If one models the circulation as a lumped vascular resistance R and a lumped arterial compliance C, then $$J = C\dot{P}^A + P^A/R$$

where $P^A$ is the aortic pressure and $\dot{P}^A$ is the first derivative of the aortic pressure. Dividing both sides of the above equation by C, one obtains $$J/C = \dot{P}^A + P^A/\tau,$$

where one defines the time constant $\tau = RC$.

The work of Bourgeois et al (cited above) is based on analysis related to this equation. Bourgeois et al showed that this equation appears to provide a valid relationship between the aortic flow J/C and the aortic pressure measured in an optimal location in the central aorta of the dog. This equation predicts the experimental decay of the aortic pressure during diastole. Bourgeois et al further demonstrated that the lumped compliance C is constant during a wide range of physiologic interventions that they applied, such as administration of vasoconstrictors, vasodilators, wide changes in heart rate, and following hemorrhage. Thus, while it may be expected that the lumped arterial compliance which primarily affects the compliance of the aorta and large arteries may vary in an individual over a time scale of years especially with the development of atherosclerotic lesions of the aorta and large arteries, the lumped arterial compliance C should not vary significantly in an individual over the time scale of days, weeks or months. The lumped arterial compliance may vary from individual to individual as a function of size, gender, age and disease processes affecting the aorta and large arteries. In the absence of disease, C could be estimated for an individual from the individual's size, gender and age.

If one now considers the aortic flow and central aortic pressure $P^A$ as digitally sampled at times $t = i\Delta$ where i is the sampling index and $\Delta$ is the sampling interval, one can express the above equation as, $$J(i)/C = (P^A(i) - P^A(i-1))/\Delta + P^A(i-1)/\tau.$$

One can further re-express the preceding equation as $$I(i) = P^A(i) - \alpha P^A(i-1)$$

where one defines $I(i) = (\Delta/C) \cdot J(i)$ and one defines $\alpha = 1 - \Delta/\tau$.

One may express $P^A$ as a function of the scaled aortic flow I $$P^A = h^A * I = \sum_{j=0}^{\infty} h(j)I(i-j)$$

here $h^A$ is an impulse response function describing the response in central aortic pressure $P^A$ to a unit impulse in the scaled flow I; * denotes the convolution operation. The impulse responses function is of the form $$h^A(j) = \alpha^j.$$

If one presumes that there is a linear relationship between the central aortic pressure $P^A$ and a peripheral arterial pressure $P^a$ then $$P^a(i) = h^a * P^A = h^a * h^A * I$$

The impulse response function $h^a$ describes the response of the peripheral arterial pressure $P^a$ to a unit impulse in $P^A$. It may be assumed that the characteristic response time of the peripheral circulation, representing the width of $h^a$, is much shorter than the characteristic response time of $h^A$ given by $1/(1-\alpha)$ (measured in units of $\Delta$).

If one further assumes that there is no energy dissipation between the site where $P^A$ is recorded and the site where $P^a$ is recorded then $h^a$ is normalized:

$$\sum_{j=0}^{\infty} h^a(j) = 1.$$

This assumption is quite reasonable in that virtually all energy dissipation occurs at the level of the microcirculation (arterioles, capillaries, venules) which are distal to the peripheral arterial recording site. The fact that $$\sum_{j=0}^{\infty} h^a(j) = 1$$

implies that the time averaged values of $P^a$ and $P^A$ are equal. One can also express I as a function of $P^a$ $$I(i) = \sum_{j=0}^{p} c(j)(P^a(i-j) - \alpha P^a(i-1-j))$$

where c(j) are the coefficients of a finite impulse length filter which is the inverse of $h^a(j)$:

$$\delta_{i0} = \sum_{j=0}^{p} c(j)h^a(i-j)$$

where $\delta_{i0}$ is the Kronecker delta function ($\delta_{i0} = 0$ unless $i = 0$ in which case $\delta_{00} = 1$).

To determine $\alpha$ one can utilize the fact that the duration of systole, the period when the aortic valve is open and during which I(i) is nonzero, and the width of $h^a$ are both narrow compared to the width of $h^A$.

Since, $$P^a(i) - \alpha P^a(i-1) = h^a * I,$$

and we wish to keep narrow the expression on the right hand side of this expression corresponding to a single beat, we may choose the value of $\alpha$ which reduces the width of the left hand side of this expression corresponding to single beats.

In general one may define the width, w, of the left hand side of this equation to be $$w = \frac{\sum_i g1(i)g2(P^a(i) - \alpha P^a(i-1))}{\sum_i g2(P^a(i) - \alpha P^a(i-1))}$$

where the sums run over values of i starting at the onset of systole of a beat and ending at the end of diastole of that same beat. The onset of systole is taken to be the point of the onset of the rapid systolic rise in $P^a(i)$ (see FIG. 2). Here g1 and g2 are increasing functions of their arguments.

If we let $g1(x) = x$ and $g2(x) = x^2$ then, we may analytically determine the value of $\alpha$ which minimizes w by requiring $$\frac{\partial w}{\partial \alpha} = 0.$$

Performing this minimization calculation, we find that the value of $\alpha$ that minimizes w is the solution to the quadratic equation $$a\alpha^2 + b\alpha + c = 0$$

where $$a = I_{01}R_{11} - R_{01}I_{11}$$

$$b = I_{11}R_{00} - I_{00}R_{11}$$

$$c = R_{01}R_{00} - I_{01}R_{00}$$

where we define $$I_{mn} = \sum_i i P^\alpha(i-m) P^\alpha(i-n)$$

$$R_{mn} = \sum_i P^\alpha(i-m) P^\alpha(i-n)$$

Having determined $\alpha$, we may now determine the coefficients c(j) for j=1 . . . p, $$I(i) = \sum_{j=0}^{p} c(j)(P^\alpha(i-j) - \alpha P^\alpha(i-1-j))$$

where $$\sum_{j=0}^{p} c(j) = 1$$

The coefficients c(j) may be determined by minimizing the error E $$E = \sum_i I^2(i)$$

where the sum runs over values of i corresponding to diastole when I should be zero because the aortic valve is closed. A least squares minimization procedure yields $$c(m) = \frac{\sum_{q=0}^{p} R^{-1}(m,q)}{\sum_{m=0}^{p} \sum_{q=0}^{p} R^{-1}(m,q)}$$

where we define the matrix R(m,q) with m=0 . . . p and q=0 . . . p $$R(m,q) = \sum_i (P^\alpha(i-m) - \alpha P^\alpha(i-m-1))(P^\alpha(i-q) - \alpha P^\alpha(i-q-1))$$

where the sum runs over values of i corresponding to diastole. $R^{-1}(m,q)$ is the inverse of the matrix R(m,q). The maximum order p may be chosen by a number of techniques well known in the art of least squares minimization.

Alternatively, one may use a transform method to determine c(m)

Defining $$\tilde{R}(m,n) = \sum_{j,k=0}^{p} R(j,k)\lambda(j,m)\lambda(k,n) \quad m,n = 0 \ldots \tilde{p}$$

$$a(n) = \frac{\sum_{m=0}^{\tilde{p}} \tilde{R}^{-1}(m,n)}{\sum_{m,n=0}^{\tilde{p}} \tilde{R}^{-1}(m,n)}$$

and $$c(j) = \sum_{n=0}^{\tilde{p}} \lambda(j,m) a(m)$$

The transformation $\lambda(j,m)$ may be given by a variety of forms. One useful form is $$\lambda(j,m) = \exp(-jm/p).$$

This transformation may allow the use of a value of $\tilde{p}$ smaller than the value of p that is needed if no transformation is applied.

To compute c(m) one must be able to calculate for a single beat the onset of diastole (this point may be estimated from the empirical formula $t_{diastole}(b) = t_{systole}(b) + \tau_\infty(1 - e^{-\beta T/\tau_\infty})$ where $T = t_{systole}(b) - t_{systole}(b-1)$, $t_{systole}(b)$ is the onset of systole of the beat number b, $t_{systole}(b)$ is the onset of systole for beat b−1, $$\tau_\infty = 0.3825$$

$$\beta = 0.7083$$

Having determined $\alpha$ and c(m) the scaled flow I(i) is given by $$I(i) = \sum_{m=0}^{p} c(m)(P^\alpha(i-m) - \alpha P^\alpha(i-1-m))$$

It may be preferable to reference $P^\alpha$ to central venous pressure or other intrathoracic pressures rather than to atmospheric pressure.

A similar analysis may be preferred where $P^\alpha$ represents a pulmonary artery pressure and I(i) represents flow across the pulmonic valve. In this case it may be preferable to reference $P^\alpha$ to pulmonary venous pressure or other intrathoracic pressures, rather than atmospheric pressure.

A computer program written in the MATLAB language (a product of The MathWorks, Inc., Natick, Mass.), which implements the algorithm described above, is provided in the Computer Program Listing Appendix, the contents of which are incorporated herein by reference in their entirety.

EXAMPLE 2

In a preferred embodiment the transforming filter is constructed utilizing two filters one of which is a nonlinear filter. First, a non-linear filter is utilized which involves computing the logarithm of the arterial blood pressure signal ($y=\ln(P_a)$) and then computing the second derivative of the resulting signal yielding $d^2y/dt^2$. In this preferred embodiment a second filter, h, is then applied to $d^2y/dt^2$ and the properties of the filter, h, adjusted to reduce the output signal from the filter during the diastolic periods. In this preferred embodiment the output signal from this second filter, $d^2z/dt^2$, will represent an estimate of the second derivative of the logarithm of the central aortic pressure ($z \cong \ln(P_A)$). The first integral of $d^2z/dt^2$, $dz/dt$, (the integration constant adjusted to set the time average of $dz/dt$ to zero) may then be computed. The value of $dz/dt$ evaluated during the diastolic periods will provide an estimate of $-1/\tau$ where $\tau$ is the central aortic decay time constant. The central aortic pressure $P_A$ may be estimated by integrating $dz/dt$ to compute the signal z and then setting $P_A \cong \exp(z)$ (the integration constant used when computed z from $dz/dt$ is determined by setting the time average of $P_A$ to the time average of $P_a$). A signal proportional to cardiac output signal may then be estimated from the equation:

$$J/C = \dot{P}^A + P^A/\tau$$

It is recognized that these and other modifications and variations of the present invention will occur to those skilled in the art and it is intended that all such modifications and variations be included within the scope of the appended claims:

What is claimed is:

1. A computer-facilitated method for visually representing to a medical practitioner a cardiac status of a patient so as to facilitate a determination by the medical practitioner of 1) a need for a cardiac-related intervention and/or 2) an effect of a prior cardiac-related, intervention, the method comprising:
   A) measuring, via a sensing device coupled to the patient, a circulatory parameter of the patient so as to provide, as an output of the sensing device, a physiologic input signal related to a circulatory pressures of the patient;
   B) electronically converting the physiologic input signal from the sensing device, via an analog-to-digital converter coupled to the sensing device, to a plurality of digital samples of the physiologic input signal related to the circulatory pressure of the patient;
   C) electronically processing at least some of the plurality of digital samples of the physiologic input signal, via at least one computer coupled to the analog-to-digital converter, to construct a transforming filter to transform the plurality of digital samples of the physiologic input signal based at least in part on one or more periods of time corresponding to diastole of the heart of the patient during which the aortic valve or the pulmonary valve of the heart of the patient is closed;
   D) electronically applying the transforming filter, via the at least one computer, to at least some of the plurality of digital samples of the physiologic input signal to compute a cardiac output signal proportional to a phasic cardiac output of the patient, the phasic cardiac output corresponding to a flow across the aortic valve or the pulmonary valve of the heart of the patient, wherein:
      the cardiac output signal has a sufficient time resolution to reflect variations in the flow across the aortic valve or the pulmonary valve within a single cardiac cycle; and
   in C), the transforming filter is constructed so that, when the transforming filter is applied in D) to the at least some of the plurality of digital samples of the physiologic input signal, the cardiac output signal is reduced during the one or more periods of time corresponding to diastole of the heart of the patient, subject to a normalization constraint on a gain of the transforming filter; and
   E) electronically displaying, on a display device coupled to the at least one computer, a visual representation of the cardiac output signal computed in D) to provide the cardiac status of the patient to the medical practitioner and thereby facilitate the determination by the medical practitioner of the need for the cardiac-related intervention and/or the effect of the prior cardiac-related intervention.

2. The method of claim 1, wherein:
   the physiologic input signal relates to a systemic arterial pressure or a pulmonary arterial pressure; and
   the normalization constraint requires that a dc gain of the transforming filter be inversely proportional to a quantity related to a corresponding systemic vascular resistance or pulmonary vascular resistance.

3. The method of claim 1, wherein C) comprises:
   C1) electronically processing the at least some of the plurality of digital samples of the physiologic input signal, via the at least one computer, to determine a quantity related to a systemic vascular resistance or a pulmonary vascular resistance of the patient, based at least in part on one or more periods of time corresponding to systole of the heart of the patient during which the aortic valve or the pulmonary value of the heart of the patient is open; and
   C2) electronically constructing, via the at least one computer, the transforming filter to transform the plurality of digital samples of the physiologic input signal based at least in part on 1) the quantity related to the systemic vascular resistance or the pulmonary vascular resistance of the patient as determined in C1) and 2) the one or more periods of time corresponding to diastole of the heart of the patient,
   wherein C1) comprises determining a value for the quantity related to the systemic vascular resistance or the pulmonary vascular resistance by:
      C1a) calculating a width of a waveform relating to the phasic cardiac output of the patient based on the at least some of the plurality of digital samples of the physiologic input signal taken over one or more cardiac cycles of the patient; and
      C1b) calculating the value for the quantity related to the systemic vascular resistance or the pulmonary vascular resistance that reduces the width of the waveform.

4. The method of claim 3, further comprising computing a value of a quantity proportional to the systemic vascular resistance or the pulmonary vascular resistance from the value of the quantity related to the systemic vascular resistance or the pulmonary vascular resistance.

5. The method of claim 4, further comprising:
   time-averaging the at least some of the plurality of digital samples of the physiologic input signal; and
   dividing the time-averaged digital samples of the physiologic input signal by the value of the quantity proportional to the systemic vascular resistance or the pulmonary vascular resistance.

6. The method of claim 4, further comprising:
   dividing the at least some of the plurality of digital samples of the physiologic input signal by the value of the quantity proportional to the systemic vascular resistance or the pulmonary vascular resistance to compute a plurality of quotient values; and time-averaging at least some of the plurality of quotient values.

7. The method of claim 4, further comprising constructing a signal proportional to vascular resistance, via the at least one computer, by repeating the step of computing the value of the quantity proportional to vascular resistance to sequential epochs of one or more cardiac cycles.

8. The method of claim 7, further comprising the step of electrically displaying, on the display device, a visual representation of the signal proportional to vascular resistance.

9. The method of claim 8, wherein the visual representation of the signal proportional to vascular resistance is displayed in real-time.

10. The method of claim 3, wherein the transforming filter implements the functional inverse of an expected cardiac-output-to-central-pressure transfer function.

11. The method of claim 3, wherein an impulse-response function of the transforming filter is the functional inverse of an exponentially decaying impulse-response function having a time constant proportional to the systemic vascular resistance or the pulmonary vascular resistance.

12. The method of claim 3, wherein the transforming filter is defined by an equation having a form:

$$y(i) = x(i) - ax(i-1)$$

where x(i) denotes an i'th sampled value of the plurality of digital samples of the physiologic input signal, x(i−1) denotes an (i−1)'th sampled value of the plurality of digital samples of the physiologic input signal, and α is the quantity related to the systemic vascular resistance or the pulmonary vascular resistance.

13. The method of claim 12, wherein x is related to a peripheral arterial pressure $P^\alpha$ of the patient as measured by the sensing device, y represents a scaled arterial flow relating to the phasic cardiac output of the patient, and the width of the waveform relating to the phasic cardiac output of the patient is given by:

$$w = \frac{\sum_i g1(i)g2(P^\alpha(i) - \alpha P^\alpha(i-1))}{\sum_i g2(P^\alpha(i) - \alpha P^\alpha(i-1))}$$

where sums over index i start at a point in time corresponding to systole beginning in the cardiac cycle, and each of g 1 and g 2 is an increasing function of a corresponding argument.

14. The method of claim 3, further comprising using the value of the quantity related to the systemic vascular resistance or the pulmonary vascular resistance to determine the dc gain of the transforming filter.

15. The method of claim 1, wherein the transforming filter is a linear filter having adjustable coefficients.

16. The method of claim 1, wherein the transforming filter is a convolution of two filters, including:

a first filter to transform at least some of the plurality of digital samples of the physiologic input signal into a central pressure signal; and a second filter to transform the central pressure signal into the cardiac output signal proportional to the phasic cardiac output.

17. The method of claim 16, wherein:

a dc gain of the first filter is constant; and the second filter has a known form based at least in part on a quantity related to a systemic vascular resistance or a pulmonary vascular resistance of the patient.

18. The method of claim 1, wherein the transforming filter is a convolution of two filters, including:

a first filter constituted by a linear filter having adjustable coefficients, wherein a dc gain of the first filter is constant; and a second filter defined by an equation having a form:

$$y(i) = x(i) - ax(i-1)$$

where α is configured to be adjusted over time based at least in part on a quantity related to a systemic vascular resistance or a pulmonary vascular resistance of the patient, x(i) denotes an i'th sampled value of the plurality of digital samples of the physiologic input signal, and x(i−1) denotes an (i−1)'th sampled value of the plurality of digital samples of the physiologic input signal.

19. The method of claim 1, wherein the physiologic input signal relates to a systemic arterial pressure or a pulmonary arterial pressure.

20. The method of claim 1, wherein:

the sensing device is noninvasively coupled to the patient; and the physiologic input signal relates to a systemic arterial pressure.

21. The method of claim 1, wherein the physiologic input signal relates to at least one of:

a peripheral arterial pressure, wherein the sensing device comprises at least one of an intra-arterial catheter and a noninvasive transducer;

a pulmonary arterial pressure, wherein the sensing device comprises an intravascular catheter; and a measurement of a volume of an ear-lobe of the patient, wherein the sensing device comprises means of measuring at least one of optical density and infra-red density of the earlobe.

22. The method of claim 1, wherein the visual representation of the cardiac output signal is at least one of a graphical representation and an alphanumerical representation.

23. The method of claim 1, wherein the visual representation of the cardiac output signal is displayed in real-time on the display device.

24. The method of claim 1, further comprising:

F) obtaining a measurement of absolute cardiac output in the patient;

G) electronically processing the cardiac output signal, via the at least one computer, to compute an average value of the cardiac output signal;

H) electronically determining, via the at least one computer, a calibration constant based at least in part on the measurement of absolute cardiac output from F) and the corresponding average value of the cardiac output signal from G); and I) electronically applying the calibration constant to the cardiac output signal to compute a normalized cardiac output signal proportional to the absolute phasic cardiac output of the patient.

25. The method of claim 1, further comprising:
electronically processing the cardiac output signal over a period of time, via the at least one computer, to compute a time-averaged value of the cardiac output signal proportional to a time-averaged phasic cardiac output of the patient.

26. The method of claim 1, wherein C comprises:
time-averaging the at least some of the plurality of digital samples of the physiologic input signal; and
constructing a modified form of the transforming filter so that, when the transforming filter is applied in D) to the time-averaged digital samples of the physiologic input signal, the cardiac output signal is proportional to a time-averaged phasic cardiac output of the patient.

27. The method of claim 1, wherein the cardiac output signal is proportional to a time-averaged phasic cardiac output.

28. The method of claim 27, wherein in E), the visual representation of the cardiac output signal is displayed in real-time.

29. The method of claim 27, further comprising the step of normalizing the cardiac output signal by using one or more independent methods of measuring absolute cardiac output.

30. The method of claim 1, wherein the circulatory pressure of the patient is referenced to atmospheric pressure, central venous pressure, pulmonary venous pressure, esophageal pressure, and/or a pressure measured in another intrathoracic location.

31. The method of claim 1, wherein each of the one or more periods of time corresponding to diastole of the heart of the patient is computed based at least in part on a first time corresponding to a preceding onset of systole of the heart of the patient and a second time corresponding to a following onset of systole of the heart of the patient.

32. The method of claim 1, wherein the transforming filter involves a nonlinear component.

33. A computer-facilitated method for visually representing to a medical practitioner a cardiac status of a patient over a sequence of one or more cardiac cycles of the heart of the patient so as to facilitate a determination by the medical practitioner of 1) a need for a cardiac-related intervention and/or 2) an effect of a prior cardiac-related intervention, the method comprising:
A) measuring, via a sensing device coupled to the patient, a circulatory parameter of the patient so as to provide, as an output of the sensing device, a physiologic input signal related to a circulatory pressure of the patient;
B) electronically converting the physiologic input signal from the sensing device, via an analog-to-digital converter coupled to the sensing device, to a plurality of digital samples of the physiologic input signal related to the circulatory pressure of the patient;
C) electronically processing at least some of the plurality of digital samples of the physiologic input signal, via at least one computer coupled to the analog-to-digital converter, to construct a transforming filter to transform the plurality of digital samples of the physiologic input signal based at least in part on one or more periods of time corresponding to diastole of the heart of the patient during which the aortic valve or the pulmonary valve of the heart of the patient is closed;
D) electronically applying the transforming filter, via the at least one computer, to at least some of the plurality of digital samples of the physiologic input signal to compute a cardiac output signal proportional to a phasic cardiac output of the patient, the phasic cardiac output corresponding to a flow across the aortic valve or the pulmonary valve of the heart of the patient, wherein:
the cardiac output signal has a sufficient time resolution to reflect variations in the flow across the aortic valve or the pulmonary valve within a single cardiac cycle; and
in C), the transforming filter is constructed so that, when the transforming filter is applied in D) to the at least some of the plurality of digital samples of the physiologic input signal, the cardiac output signal is reduced during the one or more periods of time corresponding to diastole of the heart of the patient, subject to a normalization constraint on a gain of the transforming filter;
E) electronically processing the cardiac output signal, via the at least one computer, to integrate the cardiac output signal over one or more periods of time corresponding to systole of the heart of the patient during which the aortic valve or the pulmonary valve of the heart of the patient is open, to compute a sequence of one or more values respectively proportional to one or more stroke volumes for corresponding cardiac cycles of the heart of the patient; and
F) electronically displaying, on a display device coupled to the at least one computer, a visual representation of the one or more values computed in E) and respectively proportional to the one or more stroke volumes for corresponding cardiac cycles of the heart of the patient to provide the cardiac status of the patient to the medical practitioner and thereby facilitate the determination by the medical practitioner of the need for the cardiac-related intervention and/or the effect of the prior cardiac-related intervention.

34. A system for visually representing to a medical practitioner a cardiac status of a patient so as to facilitate a determination by the medical practitioner of 1) a need for a cardiac-related intervention and/or 2) an effect of a prior cardiac-related intervention, the system comprising:
a sensing device to measure a circulatory parameter of the patient so as to provide, as an output of the sensing device, a physiologic input signal related to a circulatory pressure of the patient;
an analog-to-digital converter coupled to the sensing device to electronically convert the physiologic input signal from the sensing device to a plurality of digital samples of the physiologic input signal related to the circulatory pressure of the patient;
at least one computer coupled to the analog-to-digital converter to:
A) electronically process at least some of the plurality of digital samples of the physiologic input signal to construct a transforming filter to transform the plurality of digital samples of the physiologic input signal based at least in part on one or more periods of time corresponding to diastole of the heart of the patient during which the aortic valve or the pulmonary valve of the heart of the patient is closed; and
B) electronically apply the transforming filter to at least some of the plurality of digital samples of the physiologic input signal to compute a cardiac output signal proportional to a phasic cardiac output of the patient, the phasic cardiac output corresponding to a flow across the aortic valve or the pulmonary valve of the heart of the patient, wherein:

in B), the cardiac output signal has a sufficient time resolution to reflect variations in the flow across the aortic valve or the pulmonary valve within a single cardiac cycle; and in A), the transforming filter is constructed so that, when the transforming filter is applied to the at least some of the plurality of digital samples of the physiologic input signal in B), the cardiac output signal is reduced during the one or more periods of time corresponding to diastole of the heart of the patient, subject to a normalization constraint on a gain of the transforming filter; and a display device coupled to the at least one computer to electronically display a visual representation of the cardiac output signal computed by the at least one computer to provide the cardiac status of the patient to the medical practitioner and thereby facilitate the determination by the medical practitioner of the need for the cardiac-related intervention and/or the effect of the prior cardiac-related intervention.

35. The system of claim 34, wherein:
the physiologic input signal relates to a systemic arterial pressure or a pulmonary arterial pressure; and
the normalization constraint requires that a dc gain of the transforming filter be inversely proportional to a quantity related to a systemic vascular resistance or a pulmonary vascular resistance.

36. The system of claim 34, wherein in A) the at least one computer:
A1) electronically processes the at least some of the plurality of digital samples of the physiologic input signal to determine a quantity related to a systemic vascular resistance or a pulmonary vascular resistance of the patient, based at least in part on one or more periods corresponding to systole of the heart of the patient during which the aortic valve or the pulmonary value of the heart of the patient is open; and
A2) electronically constructs the transforming filter to transform the plurality of digital samples of the physiologic input signal based at least in part on 1) the quantity related to the systemic vascular resistance or the pulmonary vascular resistance of the patient from A1) and 2) the one or more periods of time corresponding to diastole of the heart of the patient, wherein
in A1), the at least one computer determines a value for the quantity related to the systemic vascular resistance or the pulmonary vascular resistance by:
A1a) calculating a width of a waveform relating to the phasic cardiac output of the patient based on the at least some of the plurality of digital samples of the physiologic input signal taken over one or more cardiac cycles of the patient; and
A1b) calculating the value for the quantity related to the systemic vascular resistance or the pulmonary vascular resistance that reduces the width of the waveform.

37. The system of claim 36, wherein the at least one computer computes a value of a quantity proportional to the systemic vascular resistance or the pulmonary vascular resistance from the value of the quantity related to the systemic vascular resistance or the pulmonary vascular resistance.

38. The system of claim 37, wherein the at least one computer:
time averages the at least some of the plurality of digital samples of the physiologic input signal; and
divides the time averaged digital samples of the physiologic input signal by the value of the quantity proportional to the systemic vascular resistance or the pulmonary vascular resistance.

39. The system of claim 37, wherein the at least one computer:
divides the at least some of the plurality of digital samples of the physiologic input signal by the value of the quantity proportional to the systemic vascular resistance or the pulmonary vascular resistance to compute a plurality of quotient values; and
time-averages at least some of the plurality of quotient values.

40. The system of claim 37, wherein the at least one computer:
constructs a signal proportional to vascular resistance by repeating the step of computing the value of the quantity proportional to vascular resistance to for sequential epochs of one or more cardiac cycles.

41. The system of claim 40, wherein the display device electronically displays a visual representation of the signal proportional to the systemic vascular resistance or the pulmonary vascular resistance.

42. The system of claim 41, wherein the display device displays the visual representation of the signal proportional to the systemic vascular resistance or the pulmonary vascular resistance in real-time.

43. The system of claim 36, wherein the transforming filter implements the functional inverse of an expected cardiac-output-to-central-pressure transfer function.

44. The system of claim 36, wherein an impulse-response function of the transforming filter is the functional inverse of an exponentially decaying impulse-response function having a time constant proportional to the systemic vascular resistance or the pulmonary vascular resistance.

45. The system of claim 36, wherein the transforming filter is defined by an equation having a form:

$$y(i) = x(i) - \alpha x(i-1)$$

where x(i) denotes an i'th sampled value of the plurality of digital samples of the physiologic input signal, x(i−1) denotes an (i−1)'th sampled value of the plurality of digital samples of the physiologic input signal, and α is the quantity related to the systemic vascular resistance or the pulmonary vascular resistance.

46. The system of claim 45, wherein x is related to a peripheral arterial pressure $P^a$ of the patient as measured by the sensing device, y represents a scaled arterial flow relating to the phasic cardiac output of the patient, and the width of the waveform relating to the phasic cardiac output of the patient is given by:

$$w = \frac{\sum_i g1(i) g2(P^a(i) - \alpha P^a(i-1))}{\sum_i g2(P^a(i) - \alpha P^a(i-1))}$$

where sums over index i start at a point in time corresponding to systole beginning in the cardiac cycle, and each of g1 and g2 is an increasing function of a corresponding argument.

47. The system of claim 36, wherein the at least one computer uses the value of the quantity related to the systemic vascular resistance or the pulmonary vascular resistance to determine the dc gain of the transforming filter.

48. The system of claim 34, wherein the transforming filter is a linear filter having adjustable coefficients.

49. The system of claim 34, wherein the transforming filter is a convolution of two filters, including:
   a first filter to transform at least some of the plurality of digital samples of the physiologic input signal into a central pressure signal; and
   a second filter to transform the central pressure signal into the cardiac output signal proportional to the phasic cardiac output.

50. The system of claim 49, wherein:
   a dc gain of the first filter is constant; and
   the second filter has a known form based at least in part on a quantity related to a systemic vascular resistance or a pulmonary vascular resistance of the patient.

51. The system of claim 34, wherein the transforming filter is a convolution of two filters, including:
   a first filter constituted by a linear filter having adjustable coefficients, wherein a dc gain of the first filter is constant; and
   a second filter defined by an equation having a form:

$$y(i) = x(i) - ax(i-1)$$

where α is configured to be adjusted over time based at least in part on a quantity related to the systemic vascular resistance or the pulmonary vascular resistance, x(i) denotes an i'th sampled value of the plurality of digital samples of the physiologic input signal, and x(i−1) denotes an (i−1)'th sampled value of the plurality of digital samples of the physiologic input signal.

52. The system of claim 34, wherein the physiologic input signal relates to a systemic arterial pressure or a pulmonary arterial pressure.

53. The system of claim 34, wherein:
   the sensing device is to be noninvasively coupled to the patient; and
   the physiologic input signal relates to a systemic arterial pressure.

54. The system of claim 34, wherein the physiologic input signal relates to at least one of:
   a peripheral arterial pressure, wherein the sensing device comprises at least one of an intra-arterial catheter and a noninvasive transducer;
   a pulmonary arterial pressure, wherein the sensing device comprises an intravascular catheter; and
   a measurement of a volume of an ear-lobe of the patient, wherein the sensing device comprises means of measuring at least one of optical density and infra-red density of the earlobe.

55. The system of claim 34, wherein the visual representation of the cardiac output signal is at least one of a graphical representation and an alphanumerical representation.

56. The system of claim 34, wherein the display device displays the visual representation of the cardiac output signal in real-time.

57. The system of claim 34, wherein the at least one computer:
   obtains a measurement of absolute cardiac output in the patient;
   electronically processes the cardiac output signal to compute an average value of the cardiac output signal;
   electronically determines a calibration constant based at least in part on the measurement of absolute cardiac output and the corresponding average value of the cardiac output signal; and
   electronically applies the calibration constant to the cardiac output signal to compute a normalized cardiac output signal proportional to the absolute phasic cardiac output of the patient.

58. The system of claim 34, wherein the at least one computer:
   electronically processes the cardiac output signal over a period of time to compute a time-averaged value of the cardiac output signal proportional to a time-averaged phasic cardiac output of the patient.

59. The system of claim 34, wherein the at least one computer:
   time-averages the at least some of the plurality of digital samples of the physiologic input signal; and
   constructs a modified form of the transforming filter so that, when the transforming filter is applied to the time-averaged digital samples of the physiologic input signal, the cardiac output signal is proportional to a time-averaged phasic cardiac output of the patient.

60. The system of claim 34, wherein the cardiac output signal is proportional to a time-averaged phasic cardiac output.

61. The system of claim 60, wherein in E), the visual representation of the cardiac output signal is displayed in real-time.

62. The system of claim 60, wherein the at least one computer normalizes the cardiac output signal by using one or more independent methods of measuring absolute cardiac output.

63. The system of claim 34, wherein each of the one or more periods of time corresponding to diastole of the heart of the patient is computed based at least in part on a first time corresponding to a preceding onset of systole of the heart of the patient and a second time corresponding to a following onset of systole of the heart of the patient.

64. The system of claim 34, wherein the transforming filter involves a nonlinear component.

65. A system for visually representing to a medical practitioner a cardiac status of a patient over a sequence of one or more cardiac cycles of the heart of the patient so as to facilitate a determination by the medical practitioner of 1) a need for a cardiac-related intervention and/or 2) an effect of a prior cardiac-related intervention, the system comprising:
   a sensing device to measure a circulatory parameter of the patient so as to provide, as an output of the sensing device, a physiologic input signal related to a circulatory pressure of the patient;
   an analog-to-digital converter coupled to the sensing device to electronically convert the physiologic input signal from the sensing device to a plurality of digital samples of the physiologic input signal related to the circulatory pressure of the patient;
   at least one computer coupled to the analog-to-digital converter to:
   A) electronically process at least some of the plurality of digital samples of the physiologic input signal to construct a transforming filter to transform the plurality of digital samples of the physiologic input signal based at least in part on one or more periods of time corresponding to diastole of the heart of the patient during which the aortic valve or the pulmonary valve of the heart of the patient is closed;

B) electronically apply the transforming filter to at least some of the plurality of digital samples of the physiologic input signal to compute a cardiac output signal proportional to a phasic cardiac output of the patient, the phasic cardiac output corresponding to a flow across the aortic valve or the pulmonary valve of the heart of the patient, wherein:
  in B), the cardiac output signal has a sufficient time resolution to reflect variations in the flow across the aortic valve or the pulmonary valve within a single cardiac cycle; and
  in A) the transforming filter is constructed so that, when the transforming filter is applied to the at least some of the plurality of digital samples of the physiologic input signal in B), the cardiac output signal is reduced during the one or more periods of time corresponding to diastole of the heart of the patient, subject to a normalization constraint on a gain of the transforming filter; and
C) electronically process the cardiac output signal to integrate the cardiac output signal over one or more periods of time corresponding to systole of the heart of the patient during which the aortic valve or the pulmonary valve of the heart of the patient is open, to compute a sequence of one or more values respectively proportional to one or more stroke volumes for corresponding cardiac cycles of the heart of the patient; and
a display device coupled to the at least one computer to electronically display a visual representation of the one or more values computed in C) and respectively proportional to one or more stroke volumes for corresponding cardiac cycles of the heart of the patient to the medical practitioner and thereby facilitate the determination by the medical practitioner of the need for the cardiac-related intervention and/or the effect of the prior cardiac-related intervention.

66. A computer-facilitated method for visually representing to a medical practitioner a cardiac status of a patient so as to facilitate a determination by the medical practitioner of 1) a need for a cardiac-related intervention and/or 2) an effect of a prior cardiac-related intervention, the method comprising:
  A) measuring, via a sensing device coupled to the patient, a circulatory parameter of the patient so as to provide, as an output of the sensing device, a physiologic input signal related to a circulatory pressure of the patient;
  B) electronically converting the physiologic input signal from the sensing device, via an analog-to-digital converter coupled to the sensing device, to a plurality of digital samples of the physiologic input signal related to the circulatory pressure of the patient;
  C) electronically processing at least some of the plurality of digital samples of the physiologic input signal, via at least one computer coupled to the analog-to-digital converter, to construct a transforming filter to transform the plurality of digital samples of the physiologic input signal based at least in part on one or more periods of time corresponding to diastole of the heart of the patient during which the aortic valve or the pulmonary valve of the heart of the patient is closed;
  D) electronically applying the transforming filter, via the at least one computer, to at least some of the plurality of digital samples of the physiologic input signal to compute a cardiac output signal proportional to a phasic cardiac output of the patient, the phasic cardiac output corresponding to a flow across the aortic valve or the pulmonary valve of the heart of the patient, wherein:
    the cardiac output signal has a sufficient time resolution to reflect variations in the flow across the aortic valve or the pulmonary valve within a single cardiac cycle; and
    in C), the transforming filter is constructed so that, when the transforming filter is applied in D) to the at least some of the plurality of digital samples of the physiologic input signal, the cardiac output signal is reduced during the one or more periods of time corresponding to diastole of the heart of the patient; and
  E) electronically displaying, on a display device coupled to the at least one computer, a visual representation of the cardiac output signal computed in D) to provide the cardiac status of the patient to the medical practitioner and thereby facilitate the determination by the medical practitioner of the need for the cardiac-related intervention and/or the effect of the prior cardiac-related intervention.

* * * * *